United States Patent
Taylor et al.

(10) Patent No.: US 7,390,317 B2
(45) Date of Patent: Jun. 24, 2008

(54) UNIVERSAL ACCESS SEAL

(75) Inventors: Scott Taylor, Mission Viejo, CA (US); John R Brustad, Dana Point, CA (US); Boun Pravong, Corona, CA (US); Blair Howe, deceased, late of Rancho Santa Margarita CA (US); by Judith Howe, legal representative, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 380 days.

(21) Appl. No.: 10/308,288

(22) Filed: Dec. 2, 2002

(65) Prior Publication Data

US 2004/0106942 A1 Jun. 3, 2004

(51) Int. Cl.
*A61M 5/00* (2006.01)
*A61B 17/32* (2006.01)

(52) U.S. Cl. ................... 604/167.06; 606/167
(58) Field of Classification Search ......... 606/167–185; 604/167.01, 167.03, 167.04, 167.05, 167.06
See application file for complete search history.

(56) References Cited

U.S. PATENT DOCUMENTS

| | | | |
|---|---|---|---|
| 3,818,511 A | 6/1974 | Goldberg et al. | |
| 4,403,653 A | 9/1983 | Davidson | 165/170 |
| 4,440,207 A | 4/1984 | Genatempo et al. | 150/52 R |
| 4,447,237 A | 5/1984 | Frisch et al. | 604/175 |
| 4,475,548 A | 10/1984 | Muto | 128/207.14 |
| 4,978,341 A | 12/1990 | Niederhauser | 604/167 |
| 5,053,016 A | 10/1991 | Lander | |
| 5,116,353 A | 5/1992 | Green | |
| 5,127,626 A | 7/1992 | Hilal et al. | 251/149 |
| 5,197,955 A | 3/1993 | Stephens et al. | 604/167 |
| 5,209,737 A | 5/1993 | Ritchart et al. | |
| 5,242,412 A | 9/1993 | Blake, III | |
| 5,290,245 A | 3/1994 | Dennis | |
| 5,300,036 A | 4/1994 | Mueller et al. | |
| 5,308,336 A | 5/1994 | Hart et al. | |
| 5,312,363 A | 5/1994 | Ryan et al. | 604/167 |
| 5,350,364 A | 9/1994 | Stephens et al. | 604/167 |
| 5,354,280 A | 10/1994 | Haber et al. | |
| 5,360,417 A | 11/1994 | Gravener et al. | 604/278 |
| 5,391,153 A | 2/1995 | Haber et al. | |
| 5,391,154 A | 2/1995 | Young | 604/167 |
| 5,411,483 A | 5/1995 | Loomas et al. | |

(Continued)

OTHER PUBLICATIONS

PCT International Publication No. WO98/50093 entitled Trocar Seal System. Publication Date: Nov. 12, 1998.

(Continued)

*Primary Examiner*—Vy Q. Bui
(74) *Attorney, Agent, or Firm*—Patrick Y. Ikehara; Kenneth K. Vu

(57) ABSTRACT

A surgical access device including a valve housing and an instrument receiving element mounted in the valve housing having an aperture for flexibly receiving and directing instruments having a wide range of diameters. The instrument receiving element includes a braid or mesh tube generally shaped like an hourglass. The surgical access device may include an access septum seal molded from a gel material. The surgical access device can flexibly engage instruments having diameters ranging from about 3.5 mm to about 12.9 mm.

32 Claims, 6 Drawing Sheets

U.S. PATENT DOCUMENTS

| | | | |
|---|---|---|---|
| 5,423,848 A | 6/1995 | Washizuka et al. | |
| 5,429,609 A | 7/1995 | Yoon | 604/167 |
| 5,431,676 A * | 7/1995 | Dubrul et al. | 606/185 |
| 5,453,095 A | 9/1995 | Davila et al. | 604/167 |
| 5,460,616 A | 10/1995 | Weinstein et al. | 604/167 |
| 5,492,304 A | 2/1996 | Smith et al. | |
| 5,542,931 A | 8/1996 | Gravener et al. | 604/167 |
| 5,554,124 A | 9/1996 | Alvarado | |
| 5,562,632 A | 10/1996 | Davila et al. | 604/167 |
| 5,628,732 A | 5/1997 | Antoon, Jr. et al. | |
| 5,643,301 A | 7/1997 | Mollenauer | |
| 5,645,538 A | 7/1997 | Richmond | 604/256 |
| 5,662,615 A | 9/1997 | Blake, III | 604/167 |
| 5,720,730 A | 2/1998 | Blake, III | 604/167 |
| 5,720,759 A | 2/1998 | Green et al. | |
| 5,722,958 A | 3/1998 | Gravener et al. | 604/169 |
| 5,727,770 A | 3/1998 | Dennis | |
| 5,752,938 A * | 5/1998 | Flatland et al. | 604/167.01 |
| 5,782,817 A | 7/1998 | Franzel et al. | 604/256 |
| 5,788,676 A | 8/1998 | Yoon | 604/167 |
| 5,814,026 A | 9/1998 | Yoon | 604/280 |
| 5,865,807 A | 2/1999 | Blake, III | 604/167 |
| 5,916,198 A | 6/1999 | Dillow | 604/167 |
| 5,989,233 A * | 11/1999 | Yoon | 604/523 |
| 6,127,320 A | 10/2000 | Van Ooij et al. | 508/138 |
| 6,228,061 B1 | 5/2001 | Flatland et al. | |
| 6,238,373 B1 | 5/2001 | De la Torre et al. | 604/256 |
| 6,258,065 B1 | 7/2001 | Dennis et al. | |
| 6,482,181 B1 * | 11/2002 | Racenet et al. | 604/167.06 |
| 6,551,282 B1 | 4/2003 | Exline et al. | |
| 6,595,946 B1 | 7/2003 | Pasqualucci | |
| 6,702,787 B2 | 3/2004 | Racenet et al. | |
| 6,726,663 B1 | 4/2004 | Dennis | |
| 2002/0013552 A1 | 1/2002 | Dennis et al. | |
| 2003/0004529 A1 | 1/2003 | Tsonton et al. | |
| 2004/0066008 A1 | 4/2004 | Smith | |

OTHER PUBLICATIONS

PCT International Publication No. WO98/53865 entitled Trocar Seal System. Publication Date: Dec. 3, 1998.

Laparoscopic Colorectal Surgery—Jeffrey W. Milsom, Bartholomaus Bohm; (1966) Springer-Verlag New York, Inc. p. 25.

* cited by examiner

UNIVERSAL ACCESS SEAL

BACKGROUND OF THE INVENTION

1. Field of the Invention

The present invention generally relates to surgical access devices and, more particularly, to an access seal providing passage of instrumentation and for maintaining pneumoperitoneum during laparoscopic surgeries.

2. Description of Related Art

Surgical access devices, such as a trocar 10 illustrated in FIG. 1, typically include a cannula 2 and a valve housing 4 that define a working channel 6 across a body wall 7, such as an abdominal wall, and into a body cavity 8, such as an abdominal cavity. The cannula is typically formed as an elongate rigid cylinder that is inserted, with the help of an obturator, into the body cavity to provide access across the body wall.

In a typical abdominal laparoscopic surgery, the abdomen is insufflated to pressurize and thereby enlarge the cavity within which a surgical procedure is to be performed. Various instruments used in the procedure are inserted, previously one at a time, through the working channel of the trocar to perform the surgery. In order to maintain the insufflation pressure when the instrument is inserted through the trocar, a valve has been provided in the housing to form a seal around the instrument. These instrument valves have typically been provided in the form of septum valves. When the instrument is removed, a zero-closure valve has typically been provided to seal the trocar in order to maintain the insufflation pressure. A zero-closure valve such as a double duckbill valve disclosed in U.S. Pat. No. 6,162,196, which is incorporated herein by reference, may be used.

Surgical instruments, however, vary in size and diameter. While the zero-closure valves can accommodate a relatively wide range of diameters, the septum valves are generally capable of stretching only a nominal amount to accommodate larger diameters. Specifically, the septum valves are generally formed in valve sets that are limited to the range of instruments that they can accommodate. When an instrument was required that had a diameter outside the range of a valve set, the entire trocar or at least the housing supporting the valve set had to be replaced with one that could accommodate the new instrument. In some cases, septum valves having universal seals were provided to accommodate different ranges of instrument diameters. These universal seals were typically made of elastic and tearable materials that often tear or puncture causing loss of insufflation gases. Attempts have also been made to include multiple septum seals to accommodate instruments having various diameters. For example, a septum valve may include one septum seal to engage large diameter instruments and another septum seal to engage smaller diameter instruments. These septum valves with multiple septum seals are typically more expensive to manufacture. Moreover, the seals are still limited to the specific range of instruments they can support.

Accordingly, there is a need in the art for a universal access seal capable of accommodating a wide range of instrument sizes. In particular, the universal access seal should be able to sealingly engage instruments of various diameters ranging from about 3.5 mm to about 12.9 mm. An access seal covering this range of instruments would reduce adjustments and, thus, time and costs required during surgery. It is also desirable for the universal access seal to perform when a sharp instrument is inserted off-center or when an instrument is moved radially after insertion. It is further desirable that the universal access seal facilitates the insertion and removal of instruments including tissue removal.

SUMMARY OF THE INVENTION

A surgical access device including a universal access seal is capable of accommodating instruments of various diameters. The universal access seal comprises a braid or mesh tube that is preferably shaped like an hourglass. The universal access seal can sealingly engage instruments of various diameters ranging from about 3.5 mm to about 12.9 mm. The braid facilitates insertion and manipulation of surgical instruments by directing the instruments along an axis of the surgical access device. In another embodiment of the invention, the surgical access device further includes a septum seal that is preferably molded from a gel material. The gel septum seal further facilitates the insertion and removal of instruments. These and other features and advantages of the invention will become more apparent with the description of preferred embodiments and reference to the associated drawings.

DESCRIPTION OF PREFERRED EMBODIMENTS

The following detailed description refers to the accompanying drawings that illustrate the embodiments of the present invention. Other embodiments are possible and modifications may be made to the embodiments without departing from the spirit and scope of the invention. Thus, the following detailed description is not meant to limit the invention. Rather the scope of the invention is defined by the appended claims.

Figure 1:
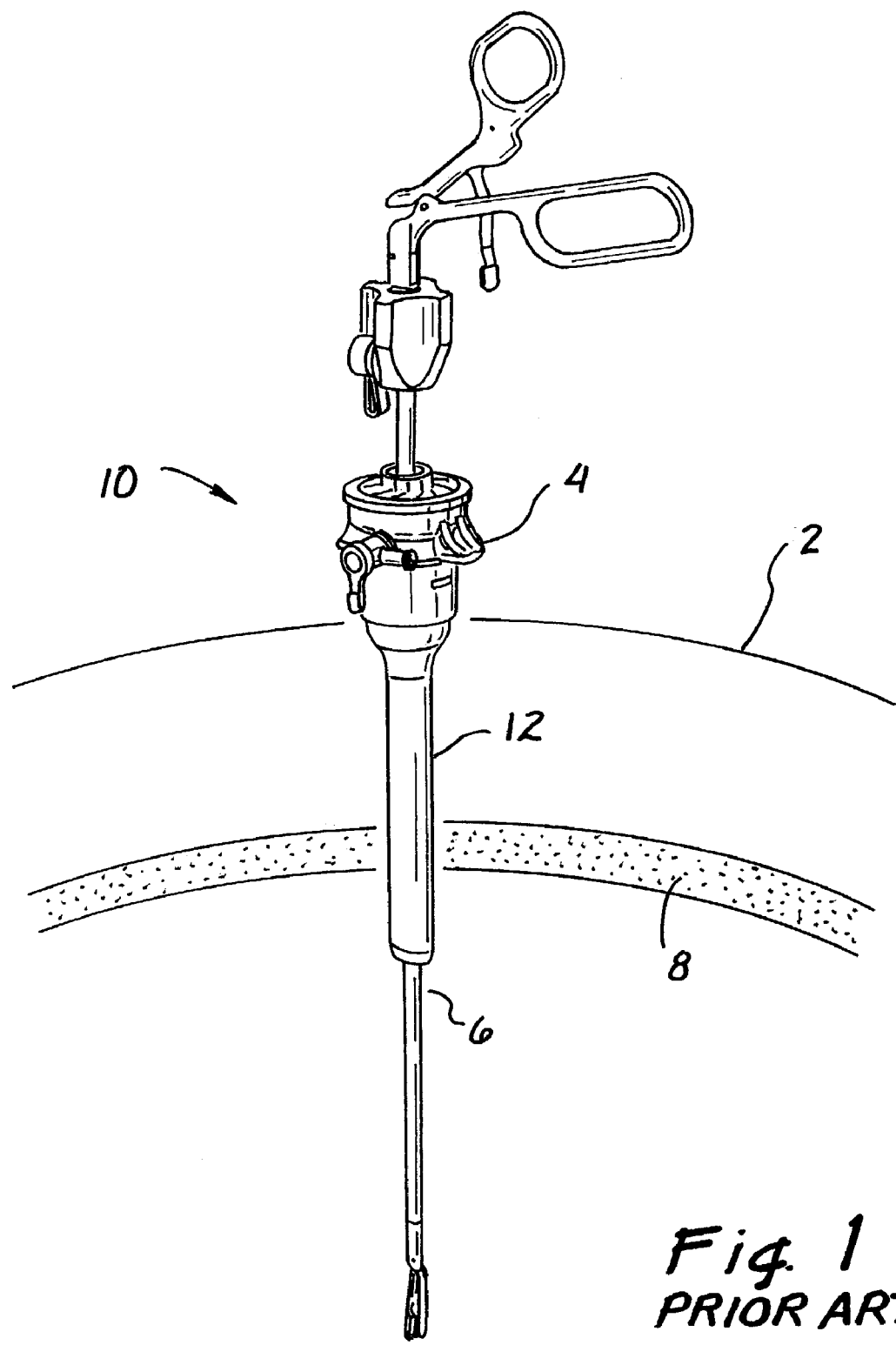
FIG. 1 illustrates a common surgical access device such as a trocar of the prior art.
Figures 2, 3:
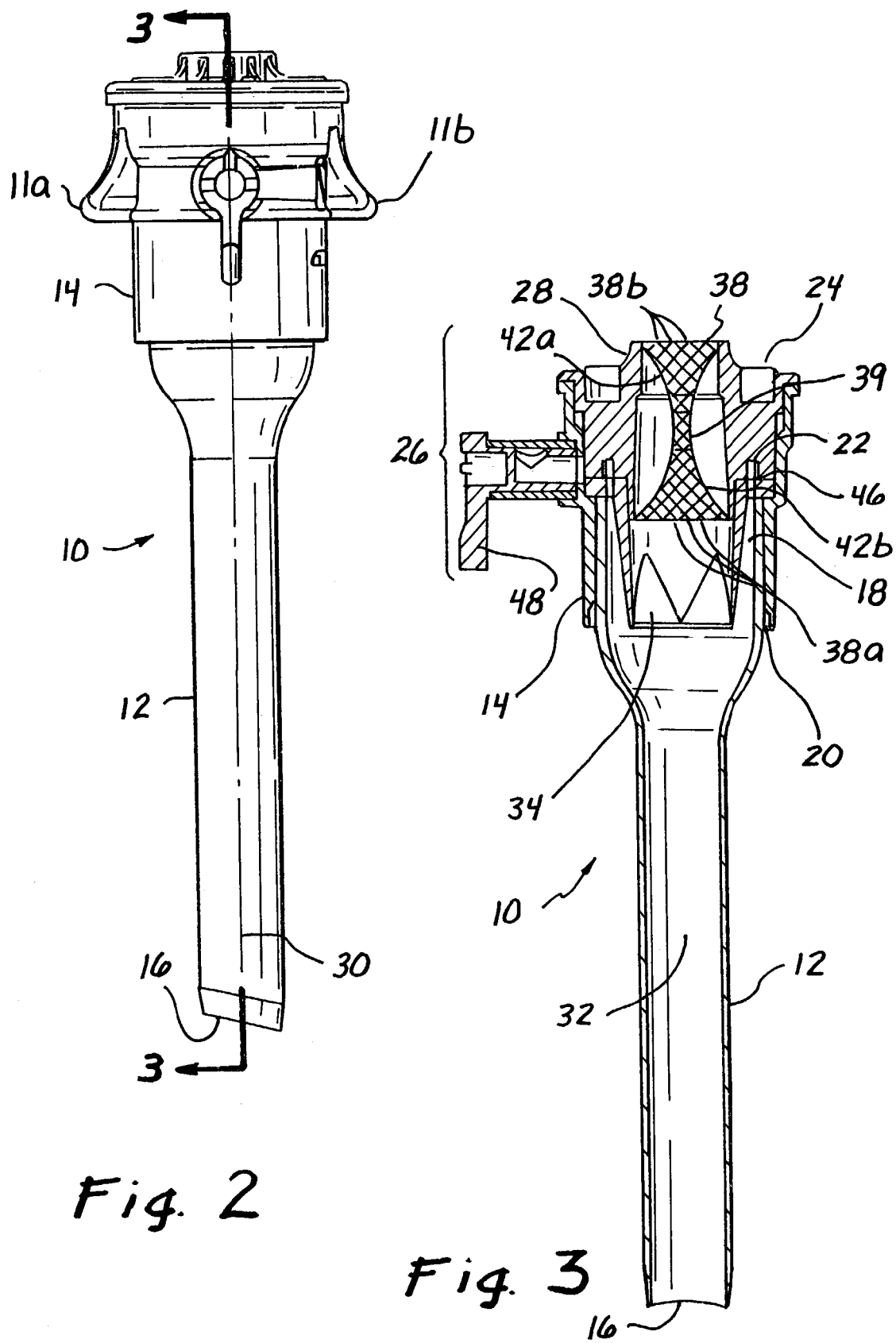
FIG. 2 illustrates a surgical access device in accordance with a first embodiment of the invention.
FIG. 3 is an axial cross-section view taken along line A-A of FIG. 2.

Referring to FIGS. 2 and 3, there is shown a first embodiment of a trocar 10 including a cannula 12 and a valve housing 14. Cannula 12 defines an interior lumen having an open distal end portion 16 and an open proximal end portion 18. Proximal end portion 18 extends into and is mounted in a distal end portion 20 of valve housing 14. Valve housing 14 has an open proximal end portion 22 that defines an opening 24. An obturator can be inserted into valve housing 14 and cannula 12 through opening 24 as further described below.

Valve housing 14 includes an access port 26, which comprises a braid or mesh tube 38 having an aperture or central sealing orifice 39 adapted to receive a wide range of instrument sizes. Access port 26 further includes an end cap 28 for mounting braid 38. End cap 28 is typically disposed in a radial plane generally perpendicular to a trocar axis 30. Braid 38 includes braid elements 38b and is preferably made of polyester, which provides a low-friction, expandable lead-in to aperture 39. Braid 38 can sealingly engage instruments inserted therethrough having diameters ranging from about 3.5 mm to about 12.9 mm. As an instrument such as an obturator is inserted into access port 26, braid 38 expands to the size of the instrument so that it forms a tight seal with the outer surface of the instrument and directs the instrument through aperture 39. By directing the instrument through aperture 39, braid 38 minimizes the possibility of tearing even if the instrument is inserted off-center or off-axis.

Braid 38 is generally shaped like an hourglass having converging and diverging sidewalls 42a and 42b, respectively, that facilitate the insertion and removal of instruments through access port 26. Braid 38 can be made from a variety of natural and synthetic monofilament thread materials including polyester, Kevlar, carbon fiber, Gore-Tex (expanded PTFE), Nomex, nylon, fiber glass, cotton, polypropylene and ceramic. Braid elements 38b, which are preferably woven from a polyester monofilament having a diameter of about 0.005", may stretch, flex, slide and/or expand in response to the direction and movement of the inserted instrument. Braid elements 38b can be made from various metal wire materials including music wire, stainless steel and Nitinol. These materials allow greater interstitial spacings within braid elements 38b that result in less contact between the inserted instrument and braid 38 to produce a more effective seal between an elastomer and the instrument as further described below.

Braid 38 can be permanently coated or treated with a variety of materials and/or processes designed to reduce friction between inserted instruments and braid 38. The coatings may be applied on each individual braid element 38b or as layers over the braid elements. The layers may be external, internal or may encapsulate braid 38. The friction reducing materials include any soft or low-durometer elastomeric material. The elastomeric material could be at least one of a thermoplastic and a thermoset. Examples of the elastomeric materials include silicone, polyurethane, polyisoprene and Kraton. Examples of other coatings and treatments include hydrophilic polymer coatings, Teflon (PTFE) coatings, cyanoacrylate coatings, Parylene coatings, plasma surface treatments and chlorination treatments.

Figure 4:
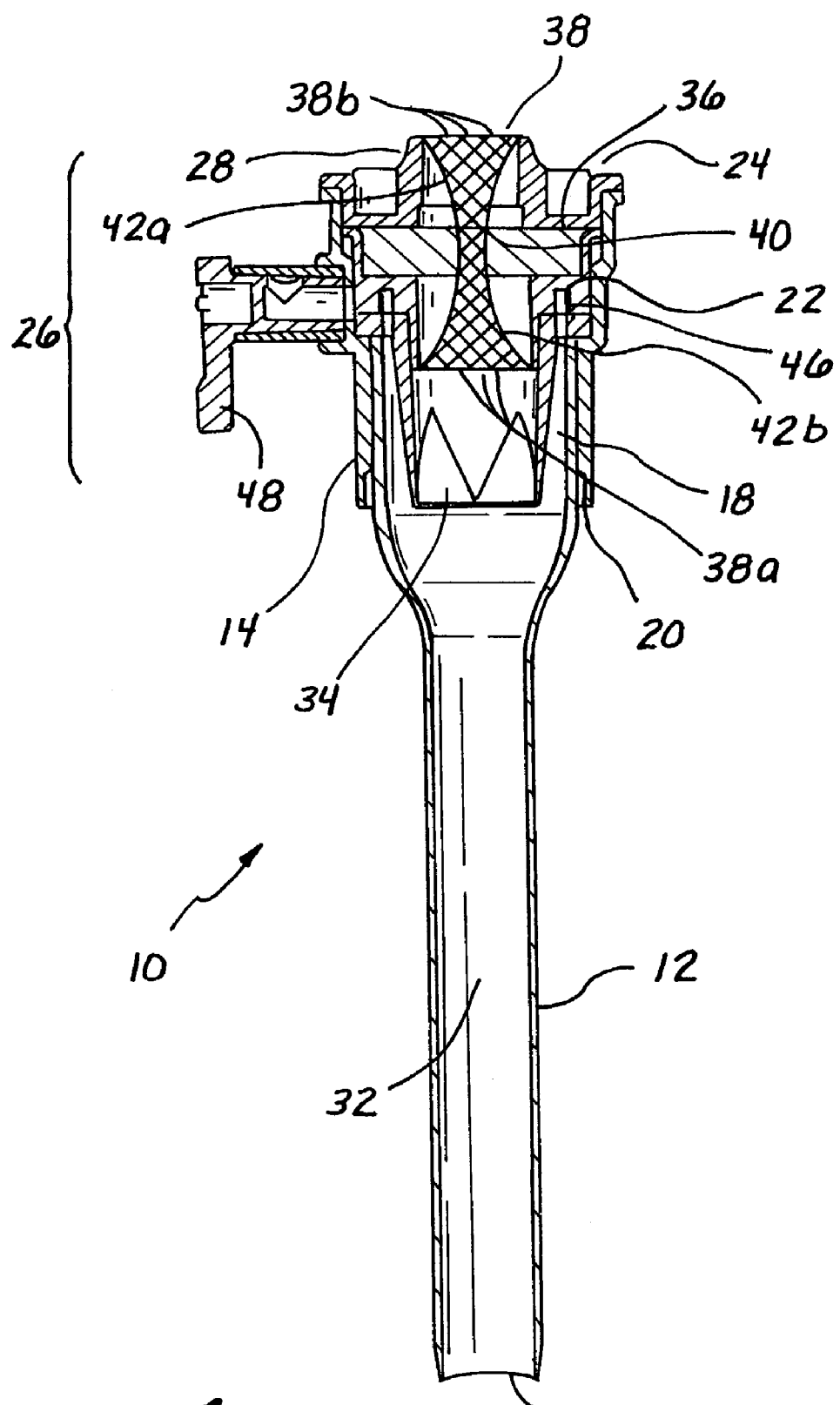
FIG. 4 illustrates a surgical access device in accordance with a second embodiment of the invention.

In a second embodiment of the invention as illustrated in FIG. 4, access port 26 further includes a septum seal 36 having an aperture 40. Aperture 40 measures about 0.115" in diameter and is in line with trocar axis 30. Braid 38 is configured to line aperture 40 of septum seal 36. Septum seal 36 may also stretch, flex, swivel and/or slide to receive the inserted instrument. Septum seal 36 may be configured to float within valve housing 14 to minimize the cat-eye effect around the inserted instrument, which can result in seal leakage during manipulation of the instrument. In another embodiment of the invention, valve housing 14 further includes finger tabs 11a and 11b providing means for engaging trocar 10 and manipulating cannula 12 into a preferred operative position. In another embodiment of the invention, access port 26 is configured as a hand-access port to allow passage of a surgeon's hand or finger into the peritoneal cavity of a patient. In another embodiment of the invention, access port 26 is utilized as a hemostasis valve for vascular or cardiovascular surgeries to prevent loss of blood yet allows passage of guidewires, catheters and other devices into the arterial or venous system of a patient. In yet another embodiment of the invention, access port 26 is utilized as an endoscopic valve for urological procedures to prevent loss of fluids yet allows passage of guidewires, catheters and other devices into the urethra or ureter.

Septum seal 36 is preferably molded from a gel material and is preferably encased in a seal housing to affect a radial compressive force about the outside diameter of septum seal 36. As an instrument is inserted into braid 38, braid 38 expands while septum seal 36 resists expansion due to the outer compressive force provided by the seal housing. This forces the gel material to extrude through interstitial spaces 38a to sealingly engage the outside diameter of any instrument inserted through access port 26 while minimizing the frictional contact between the inserted instrument and septum seal 36. The gel material has a low durometer that enables it to extrude through interstitial spaces 38a. The gel material is preferably a composite material comprising mineral oil and a thermoplastic elastomer such as a Kraton material.

Septum seal 36 could also be manufactured from a closed cell foam material or an open cell foam material sealed with a film coating. Examples of the foamed materials include silicone, urethane, Kraton, polyethylene, polyisoprene, polyvinylchloride (PVC), polyurethane, ethylene propylene diene monomer (EPDM), Neoprene and styrene butadiene (SBR). Septum seal 36 may be coated or treated with a variety of materials and/or processes designed to reduce friction between the inserted instruments and the gel material. Examples include hydrophilic polymer coatings, Teflon (PTFE) coatings, thermoplastic coatings, cyanoacrylate coatings, Parylene coatings, plasma surface treatments, cornstarch powder coatings and chlorination treatments. Septum seal 36 may also be lubricated with a variety of materials to facilitate the insertion and withdrawal of instruments. Examples of these materials include silicone oil, silicone grease, liquid soaps, Astroglide lubricants, mineral oil, glycerin, alcohol, saline, Teflon (PTFE) lubricants, Krytox lubricants, molybdenum disulfide lubricants and graphite.

Another aspect of the invention is braid elements 38b also serve to reduce the force required to insert and advance an instrument through septum seal 36. The coefficient of kinetic friction (f) for polyester braid 38/septum seal 36 verses a metal or polymer instrument shaft is significantly less than that of an elastomeric septum seal verses a metal or polymer instrument shaft. Typical coefficient of kinetic friction values range from about 0.15 to about 0.5 for polymers such as polyester verses steel, whereas the typical coefficient of kinetic friction values for elastomers verses steel range from about 1.6 to about 10. As a result, braid elements 38b minimize the contact between the shaft of the inserted instrument and septum seal 36 and minimize the frictional forces required to insert and advance the instrument through septum seal 36.

Braid elements 38b also serve to capture lubricants such as oils and greases within interstitial spaces 38a. In particular, interstitial spaces 38a capture lubricants to prevent inserting instruments from wiping all of the lubricants from braid 38 and septum seal 36 during instrument exchanges. That is, some lubricant will always be present within braid elements 38b to facilitate manipulation and exchange of instruments throughout the surgical procedure. The presence of lubricants also improves the sealing properties of the present invention. As observed with prior art trocar seals, lubricants such as oils and greases are typically completely transferred from the lubricated septum seals to the inserted instruments after a few instrument exchanges resulting in a non-lubricated septum seal for the remainder of the surgical procedure. A drawback of the prior art seals is subsequent instrument manipulations and exchanges become increasingly difficult for the operating surgeon or user.

With the flexibility of the braid and septum seal of the invention, an instrument having a sharp, irregular, forked or otherwise potentially damaging distal features may be directed through the access port in a minimally threatening position. The braid, either alone or in combination with the septum seal, can stretch, flex, slide and/or expand so as to easily receive an approaching instrument. The flexibility of the braid and septum seal thus provides a very durable and relatively friction-free insertion and removal of instrumentation.

Access port 26 may further comprise a zero-closure valve 34 such as a double duckbill valve, which maintains pneumoperitoneum in the absence of inserted instrumentation as described in the incorporated U.S. Pat. No. 6,162,196. With this embodiment, valve housing 14 and cannula 12 extend along trocar axis 30 and define a working channel 32 for receipt of a surgical instrument. In the absence of an instrument, zero-closure valve 34 closes on itself forming a gas-tight seal at very low retrograde pressure and preventing loss of insufflation gas. When an instrument is present in working channel 32, braid 38 and/or septum seal 36 forms a seal with the instrument in order to seal working channel 32. In particular, access port 26 provides a positive seal with respect to instruments inserted therethrough.

Figure 6:
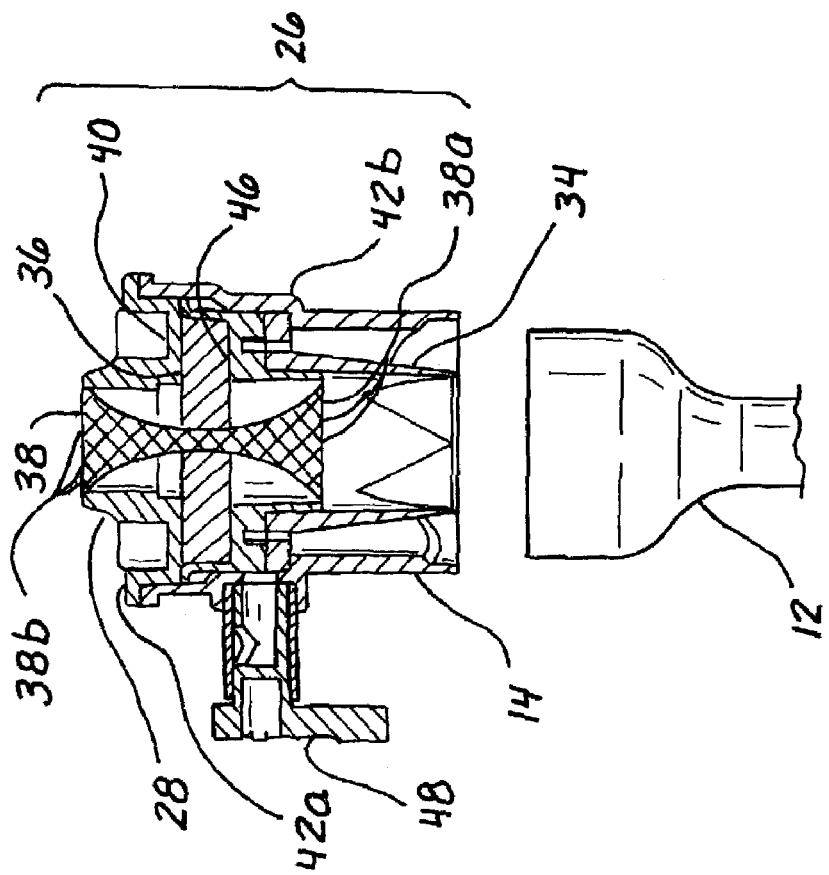
FIG. 6 is an axial cross-section view taken along line B-B of FIG. 5.
Figure 5:
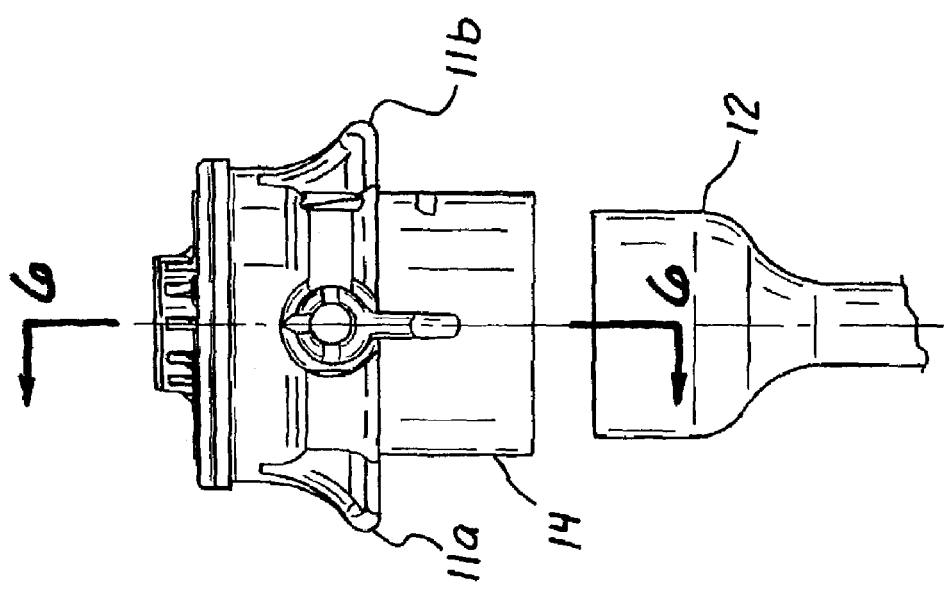
FIG. 5 illustrates a valve housing of the surgical access device of the invention.

Access port 26 may further comprise a manifold 46 and a stopcock 48, both of which are preferably molded from polycarbonate. Manifold 46 is positioned within valve housing 14 and serves to locate zero-closure valve 34 and septum seal 36 relative to valve housing 14. Manifold 46 also facilitates the flow of insufflation gasses from an insufflator, through cannula 12 and into the surgical site. End cap 28 is preferably ultrasonically welded to valve housing 14 and serves to fix manifold 46, zero-closure valve 34, septum seal 36 and braid 38 within valve housing 14. The proximal end of braid 38 is preferably bonded to end cap 28 and the distal end of braid 38 is not attached to any component and is free to float within access port 26. Braid 38 is preferably flared at both the proximal end and the distal end in an hourglass shape. In another embodiment of the invention, the proximal end of braid 38 is bonded or fixed to manifold 46 to prevent migration during instrument insertion and removal. Zero-closure valve 34 is preferably molded from polyisoprene and is located distal to septum seal 36. As illustrated in FIGS. 5 and 6, valve housing 14 including access port 26 may be removably attached to a disposable or reusable cannula 12.

The following describes the preferred method of manufacturing an access port in accordance with an embodiment of the invention. Zero-closure valve 34, which is preferably transfer molded, is first placed into valve housing 14, which is preferably injection molded. Manifold 46, which is preferably injection molded, is then mounted on top of zero-closure valve 34. Septum seal 36, which is preferably injection molded, is then placed on top of manifold 46. Braid 38, which is preferably heat set to form flared sections at its proximal and distal ends, is then bonded to end cap 28, which is preferably injection molded. The distal end of braid 38 is then threaded through aperture 40 of septum seal 36, and end cap 28 is positioned on top of valve housing 14 to effectively capture all of the access port components. End cap 28 is then ultrasonically welded to valve housing 14. Stopcock 48 is then bonded to valve housing 14. The housing assembly is then removably attached, via bayonet locks, to cannula 12, which is preferably injection molded from polycarbonate.

Figure 7:
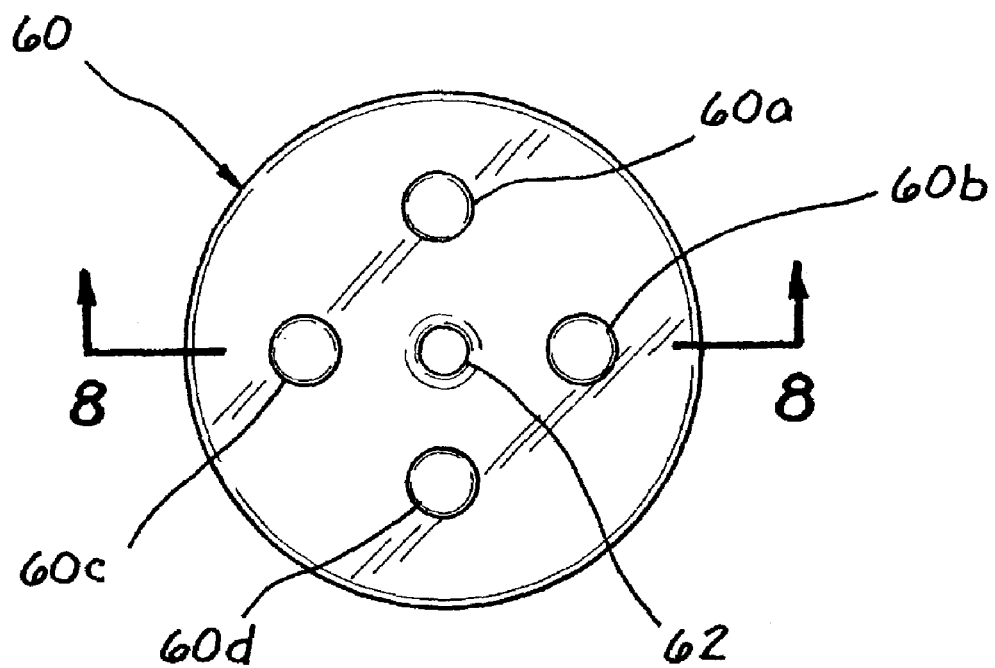
FIG. 7 illustrates a valve septum seal of a surgical access device in accordance with another embodiment of the invention.
Figure 8:
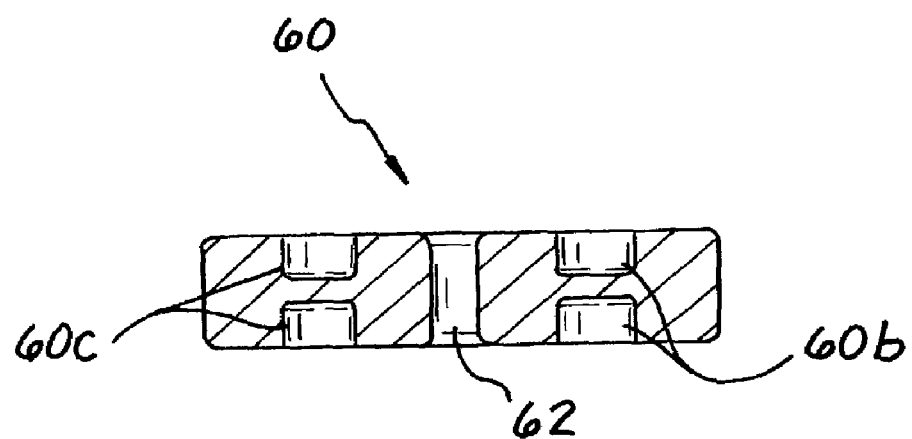
FIG. 8 is an axial cross-section view taken along line C-C of FIG. 7.
Figure 9:
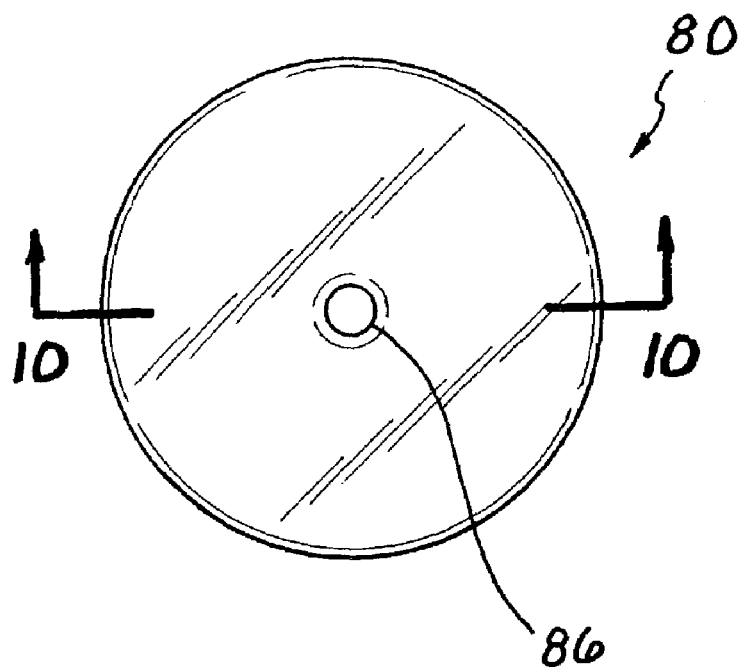
FIG. 9 illustrates a valve septum seal of a surgical access device in accordance with another embodiment of the invention.
Figure 10:
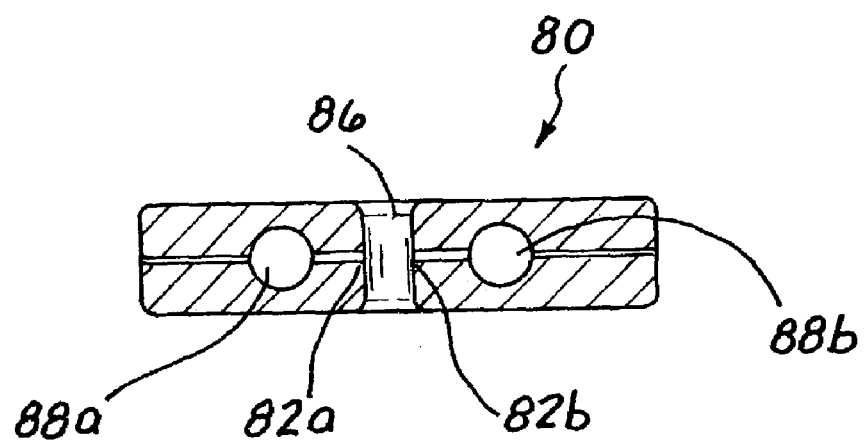
FIG. 10 is an axial cross-section view taken along line D-D of FIG. 9.

In another embodiment of the invention, FIGS. 7 and 8 illustrate a septum seal 60 comprising a plurality of cored sections 60a-60d spaced about a central aperture 62 that enable septum seal 60 to deform in response to insertion of an instrument. Cored sections 60a-60d may be formed in either or both of the top and bottom surfaces of septum seal 60 as illustrated in cross-section view C-C in FIG. 8. In yet another embodiment of the invention, FIGS. 9 and 10 illustrate a septum seal 80 comprising a plurality of small apertures 82a and 82b connected to pockets 88a and 88b, respectively. Small apertures 82a and 82b are in fluid communication with and are oriented perpendicular to instrument insertion aperture 86. Pockets 88a and 88b are located within septum seal 80 and serve to store lubricants. When an instrument is inserted through aperture 86, septum seal 80 deforms forcing the lubricants to ooze from storage pockets 88a and 88b through apertures 82a and 82b, respectively, thereby lubricating the instrument and facilitating its insertion and manipulation.

It is appreciated that various fillers and additives could be incorporated into the various elastomeric septum seal materials to reduce the tackiness and to increase the lubricity of the material thereby facilitating the insertion and removal of instruments. Examples of the additives include waxes, soaps, paraffin wax, beeswax, calcium stearate, stearic acid, silicone oil, silicone grease, mineral oil, glycerin, graphite, silica, glass spheres, Teflon (PTFE), Parylene, talc and molybdenum disulfide.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention.

The invention claimed is:

1. A surgical access device operatively connected to a cannula having an axis extending between a proximal end and a distal end, comprising:
 a valve housing disposed at the proximal end of the cannula; and
 an instrument receiving element mounted in the valve housing having an aperture for flexibly receiving and directing instruments having a wide range of diameters;
 an end cap mounting the instrument receiving element and having a proximal end away from the proximal end of the cannula and a distal end coupled to the valve housing;
 a zero-closure valve positioned within the valve housing;
 wherein the instrument receiving element includes a mesh tube extending from the proximal end of the end cap and into a portion of the zero-closure valve.

2. The surgical access device recited in claim 1, further comprising an access septum seal disposed in the valve housing having a septum seal aperture.

3. The surgical access device recited in claim 2, wherein the access septum seal is molded from a gel material.

4. The surgical access device recited in claim 3, wherein the gel material extrudes through interstitial spaces of the instrument receiving element sealingly engaging an instrument while minimizing frictional contact between the instrument and the access septum seal.

5. The surgical access device recited in claim 3, wherein the gel material is a composite material comprising mineral oil and a thermoplastic elastomer.

6. The surgical access device recited in claim 3, wherein the gel material comprises a soft or low-durometer elastomeric material that is at least one of a thermoplastic and a thermoset.

7. The surgical access device recited in claim 6, wherein the elastomeric material includes at least one of silicone, polyurethane, polyisoprene and Kraton.

8. The surgical access device recited in claim 3, wherein the gel material comprises a closed cell foam material or an open cell foam material.

9. The surgical access device recited in claim 8, wherein the foam material includes at least one of silicone, urethane, Kraton, polyethylene, polyisoprene, polyvinylchloride (PVC), polyurethane, ethylene propylene diene monomer (EPDM), Neoprene and styrene butadiene (SBR).

10. The surgical access device recited in claim 1, wherein the instrument receiving element includes a tubular braid.

11. The surgical access device recited in claim 10, wherein the braid is coated with a material for reducing friction.

12. The surgical access device recited in claim 11, wherein the coating includes any soft or low-durometer elastomeric material.

13. The surgical access device recited in claim 12, wherein the elastomeric material includes at least one of a thermoplastic and a thermoset.

14. The surgical access device recited in claim 12, wherein the elastomeric material includes at least one of silicone, polyurethane, polyisoprene and Kraton.

15. The surgical access device recited in claim 11, wherein the coating includes at least one of hydrophilic polymer coating, Teflon (PTFE) coating, cyanoacrylate coating and Parylene coating.

16. The surgical access device recited in claim 11, wherein the coated braid expands to form a seal around an outer surface of an instrument.

17. The surgical access device recited in claim 10, wherein the braid is treated with at least one of plasma surface treatment and chlorination treatment for reducing friction during passage of instrumentation.

18. The surgical access device recited in claim 10, wherein the braid further comprises braid elements.

19. The surgical access device recited in claim 18, wherein the braid elements comprise a metal wire material including music wire, stainless steel and Nitinol.

20. The surgical access device recited in claim 18, wherein the braid elements provide interstitial spaces between an inserted instrument and the braid.

21. The surgical access device recited in claim 20, wherein the braid elements capture lubricants within the interstitial spaces to facilitate manipulation and exchange of instruments.

22. The surgical access device recited in claim 10, wherein the braid comprises at least one of natural and synthetic monofilament thread materials including polyester, Kevlar, carbon fiber, Gore-Tex (expanded PTFE), Nomex, nylon, fiber glass, cotton, polypropylene and ceramic.

23. The surgical access device recited in claim 1, wherein the mesh tube includes a converging sidewall, a diverging sidewall and a center portion, the converging sidewall inwardly tapering at an angle to a center portion and the diverging sidewall outwardly extending at an angle from the center portion.

24. The surgical access device recited in claim 1, wherein the instrument receiving element is generally shaped like an hourglass.

25. The surgical access device recited in claim 24, wherein the instrument receiving element includes a converging sidewall facilitating insertion of an instrument and a diverging sidewall facilitating removal of the instrument.

26. The surgical access device recited in claim 1, wherein the range of diameters is from about 3.5 mm to about 12.9 mm.

27. The surgical access device recited in claim 1, further comprising a zero-closure valve disposed in the valve housing.

28. The surgical access device recited in claim 1, wherein the valve housing further comprises means for manipulating the cannula to a preferred operative position.

29. The surgical access device recited in claim 28, wherein the manipulating means includes finger tabs.

30. The surgical access device recited in claim 1, wherein the valve housing is configured as a hand-access port allowing passage of a user's hand or finger into a body conduit or cavity.

31. The surgical access device recited in claim 1, further comprising a stopcock.

32. The trocar recited in claim 1 wherein one end of the mesh tube is fixed to the proximal end of the end cap and an opposing end of the mesh tube positioned within a portion of the zero-closure valve is unattached.

* * * * *